United States Patent [19]

Oda et al.

[11] Patent Number: 4,763,876
[45] Date of Patent: Aug. 16, 1988

[54] VALVE SEAT INSERT AND CYLINDER HEAD WITH THE VALVE SEAT INSERT

[75] Inventors: Isao Oda, Nagoya; Nobuo Tsuno, Kasugai, both of Japan

[73] Assignee: NGK Insulators, Ltd., Japan

[21] Appl. No.: 926,520

[22] Filed: Nov. 4, 1986

[30] Foreign Application Priority Data

Nov. 5, 1985 [JP] Japan .................. 60-246288

[51] Int. Cl.$^4$ .............................................. F01L 3/00
[52] U.S. Cl. ..................................... 251/359; 251/368; 123/188 S
[58] Field of Search ................... 123/188 S; 251/359, 251/368

[56] References Cited

U.S. PATENT DOCUMENTS

| | | | |
|---|---|---|---|
| 1,949,613 | 3/1934 | McDonald | 123/188 S |
| 2,447,858 | 8/1948 | Hoern | 123/188 S |
| 2,665,675 | 1/1954 | Sheppard | 123/188 S |
| 2,695,628 | 11/1954 | Wheildon, Jr. | 137/533.11 |
| 2,753,858 | 7/1956 | Honeyman et al. | 123/188 S |
| 2,753,859 | 7/1956 | Bartlett | 123/188 S |
| 3,487,823 | 1/1970 | Tarten et al. | 251/359 |
| 3,658,295 | 4/1972 | Paine et al. | 251/360 |
| 3,871,616 | 3/1975 | Taylor | 251/175 |
| 4,546,737 | 10/1985 | Kazuoka et al. | 123/188 S |
| 4,554,897 | 11/1985 | Yamada et al. | 123/188 S |
| 4,556,022 | 12/1985 | Yamada et al. | 123/188 S |

FOREIGN PATENT DOCUMENTS 3506069  9/1985  Fed. Rep. of Germany.
60-104707  6/1985  Japan.

OTHER PUBLICATIONS

Ingenieurs De L'Automobile, No. 8, Nov.-Dec. 6, 1983, pp. 28-33, Paris, France; U. Dworak et al.; "Ceramic Components for Combustion Engines".

*Primary Examiner*—A. Michael Chambers
*Attorney, Agent, or Firm*—Parkhurst & Oliff

[57] ABSTRACT

A valve seat insert for use in a cylinder head a a piston engine including a ceramic member having a valve seat surface and a metallic member integrally combined on the outer periphery of the ceramic member. The metallic member is made of a metallic material having a coefficient of thermal expansion the same as or higher than that of the ceramic member and lower than that of the material of the cylinder head. The valve seat insert has not only high wear resistivity, heat shock resistivity and heat resistivity, but also easy productivity and reliability for use and further possible to be handled and fitted into the cylinder head easily. A cylinder head for piston engine has the above valve seat incorporated therein.

8 Claims, 2 Drawing Sheets

FIG_1
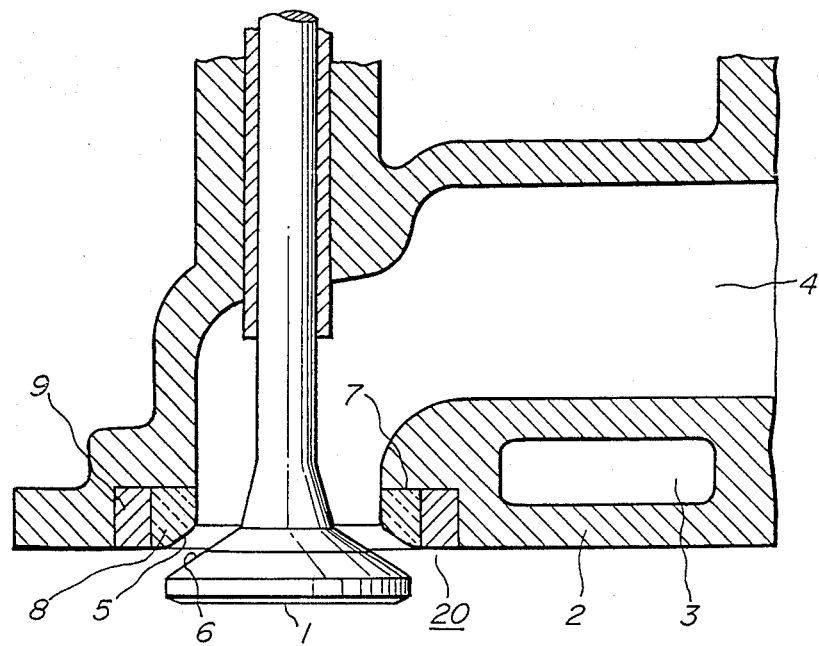

FIG_2
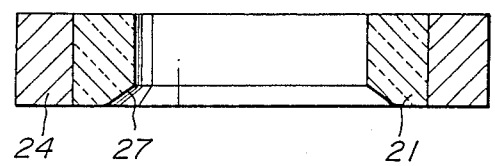
FIG_3
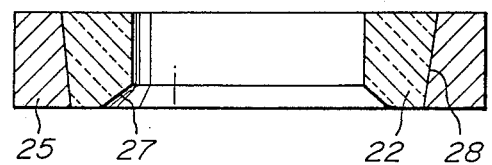
FIG_4
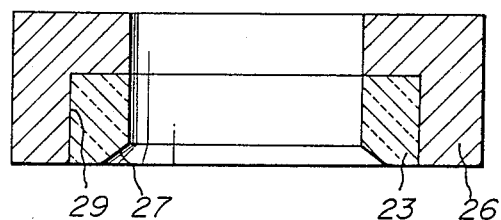
FIG_5
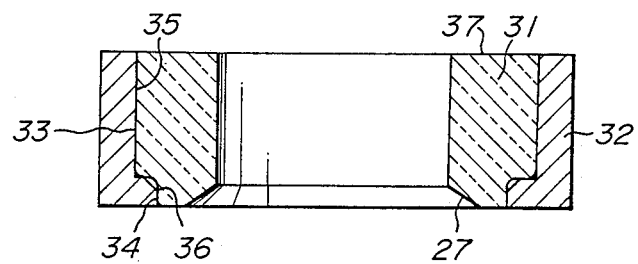

VALVE SEAT INSERT AND CYLINDER HEAD WITH THE VALVE SEAT INSERT

BACKGROUND OF THE INVENTION

1. Field of the Invention

The present invention relates to a valve seat insert to be used in cylinder heads for piston engines and a cylinder head with the valve seat insert, in particular, to a combined valve seat insert consisting of a ceramic member and a metallic member and a cylinder head for a piston engine with the combined valve seat insert.

The valve seat insert is a cylindrical or ring shaped member and is used by securely fitting to the valve seating portion of the cylinder head of a piston engine in order to keep a pressure in the cylinder when a valve is seated on the seat insert.

2. Related Art Statement

Heretofore, valve seat inserts entirely made of ceramic material have been proposed in view of high wear resistivity and heat resistivity, as shown in Japanese Patent Application Laid-open Publication No. 59-162345 and Japanese Utility Model Application Laid-open Publication No. 60-12603.

The Japanese Patent Application Laid-open Publication No. 59-162345 discloses a valve seat made of partial stabilized zirconia (PSZ), while the Japanese Utility Jodel Application Laid-open Publication No. 60-12603 discloses a valve seat made of ceramic material for performing a part of a combustion chamber and a shock absorbing mechanism for releasing an impact load caused by striking a valve made of ceramic material against the valve seat.

The partial stabilized zirconia disclosed in the Japanese Patent Application Laid-open Publication No. 59-162345 has a low heat conductivity and a high heat insulating characteristic, but has a high heat expansion coefficient so that when the valve seat entirely made of partial stabilized zirconia is used under a condition wherein a temperature gradient exists, the valve seat will be destroyed by heat stress. Furthermore, the valve seat entirely made of ceramic material must be carefully handled when fitting into the cylinder head since the ceramic material lacks toughness. While, the valve seat disclosed in the Japanese Utility Model Laid-open Publication No. 60-12603 is entirely made of ceramic material and has a complicated shape in order to accommodate the shock absorbing mechanism. Such a complicated valve seat is difficult to product and has a problem in reliance for use, since ceramic material is difficult to machine and lacks toughness. Furthermore, such a valve seat entirely made of ceramic material is difficult to assemble automatically since ceramic material lacks toughness and requires careful handling when fitting into the cylinder head.

In general, the cylinder head is made of metallic material having a coefficient of thermal expansion higher than that of ceramic. Therefore, when the cylinder head provided with the valve seat entirely made of ceramic is heated, the combined strength between the cylinder head and the valve seat is decreased by the difference of the thermal expansion thus resulting in the valve seat comes loosening and falling out of position.

It can be understood from the above that the valve seat whole of which is made of ceramic is not practicable.

SUMMARY OF THE INVENTION

An object of the present invention is to provide a valve seat insert having not only high wear resistivity, heat shock resistivity and heat resistivity, but also easy productivity and reliability for use and further possible to be handled and fitted into the cylinder head easily.

Another object of the present invention is to provide a cylinder head provided with the aforementioned valve seat insert.

According to the present invention, for accomplishing the above objects, the valve seat insert comprises a ceramic member having a valve seating face and a metallic member integrally combined on the outer periphery of the ceramic member. The metallic member is made of metallic material having a coefficient of thermal expansion which is the same as or high than that of the ceramic member and lower than that of the material of the cylinder head. The ceramic member and the metallic member may be cylindrical. The ceramic member may be tapered at the outer wall.

According to another aspect of the present invention, a cylinder head for piston engines comprises a valve seat insert adapted for seating a valve of the piston engine, the valve seat insert consisting of a ceramic member having a vlave seat surface and a metallic member integrally formed on the outer periphery of the ceramic member, the metallic member having a coefficient of thermal expansion which is the same as or higher than that of the ceramic member and lower than that of the material of the cylinder head.

The ceramic member forming one portion of the valve seat insert of the present invention may be made of an oxide type ceramic and/or a nonoxide type ceramic. The oxide type ceramics are preferably partially stabilized zirconia and alumina and the nonoxide type ceramics are preferably silicon nitride, silicon carbide and sialon, but in view of high wear resistivity, heat shock resistivity and heat resistivity, particularly the ceramic member is preferably made of at least one ceramic material selected from the group of silicon nitride, silicon carbide and sialon.

The metallic member forming another portion of the valve seat insert is preferably made of metallic material having a coefficient of thermal expansion which is the same as or higher than that of the above mentioned ceramic material and lower than that of the material of the cylinder head and also having high mechanical strength at high temperature.

Such type of metals are, for example, Fe-Ni alloys, Fe-Ni-Co alloys, Ti and Ti alloys, refractory metals and their alloys, and stinless steels. Fe-Ni alloys include alloys having a low coefficient of thermal expansion such as 42 Ni-Fe alloy and 52 Ni-Fe alloy mainly consisting of Ni and Fe and Invar mainly consisting of Ni and containing few other alloy elements. Fe-Ni-Co alloys also include alloys having a low coefficient of thermal expansion such as Kovar and Super Invar mainly consisting of Ni, Fe and Co and Incoloy 903 mainly consisting of Ni, Fe, Co and containing few other alloy elements. The stainless steel is of a low coefficient of thermal expansion such as ferritic stainless steel, martensitic stainless steel and precipitation hardening stainless steel.

Further, cylinder heads are generally made of material having a coefficient of thermal expansion higher than $10 \times 10^{-6}/°C$. such as aluminum alloys, cast iron and low alloy steels.

Then, the ceramic material and the metallic material usable for the valve seat insert of the present invention and their coefficients of thermal expansion are shown in the following Table.

and the metallic member may be appropriately decided in according to kind of material to be used, temperature in use, methods of combining both members or the shape of the members.

TABLE

| Material | Composition (main) | Coefficient* of thermal expansion | Temperature range | Note |
| --- | --- | --- | --- | --- |
| Silicon nitride | $Si_3N_4$ | 3.3 | 40~1000° C. | Pressureless sintering |
| Silicon carbide | SiC | 4.3 | 40~1000° C. | Pressureless sintering |
| Sialon | | 3.4 | 0~1200° C. | |
| Zirconia | $ZrO_2$ (partial stabilized) | 10.5 | 40~1000° C. | Pressureless sintering |
| Alumina | $Al_2O_3$ | 8.1 | 40~1000° C. | Pressureless sintering |
| 42Ni—Fe alloy | Fe—42Ni | 7.5~8.5 | 20~500° C. | |
| 52Ni—Fe alloy | Fe—50Ni | 9.5~10.8 | 20~500° C. | |
| Invar | Fe—36Ni | 9.0~10.5 | 20~500° C. | |
| Kovar | Fe—29Ni—17Co | 5.7~6.5 | 20~500° C. | |
| Incoloy 903 | Fe—38Ni—16Co—3Nb—1.5Ti | 7.4~8.3 | 20~500° C. | |
| Ferritic stainless steel | Fe—17Cr—1Mn—1Si | 9.3 | 20~100° C. | SUS 436 |
| Martensitic stainless steel | Fe—13Cr | 11.6 | 20~500° C. | SUS 416 |
| Precipitation hardening stainless steel | Fe—15Cr—7Ni—3Mo | 11.4 | 20~300° C. | PH15—7Mo |
| Nb alloy | Nb—10Hf—1Ta | 8.1 | 20~1200° C. | Refractory metal alloy |
| Nb alloy | Nb—10W—2.5Zr | 7.4 | 20~1200° C. | Refractory metal alloy |
| Ta alloy | Ta—10W | 6.7 | 20~1650° C. | Refractory metal alloy |
| Mo alloy | Mo—0.5Ti | 6.1 | 20~1000° C. | Refractory metal alloy |
| Titanium | Ti | 9.5 | 20~500° C. | |
| Titanium-alloy | Ti—6Al—4V | 9.8 | 20~500° C. | |

Note:
Each coefficient of thermal expansion of the material shows values at the temperature (max 550~600° C.) or the neighbor in use of the valve seat insert.
*Unit: $10^{-6}$/°C.

It will be seen from the table that the coefficient of thermal expansion of the ceramic materials are in the range of $3\sim 11\times 10^{-6}$/°C., while the coefficient of thermal expansion of the metallic materials are in the range of $5\sim 12\times 10^{-6}$/°C.

Therefore, a reliable combination of materials usable for the ceramic member and the metallic member of the valve seat insert of the present invention is decided in consideration of the coefficient of thermal expansion of the material of the cylinder head to satisfy the above mentioned condition such that the metallic member has a coefficient of thermal expansion which is the same as or higher than that of the ceramic member and lower than that of the material of the cylinder head.

The valve seat insert of the present invention is not limited to a specified shape, but is usually constructed in an integral combined form of an inner cylindrical ceramic member and an outer cylindrical metallic member. The ceramic member has a slanted valve seat surface at one end of the inner wall thereof for closely contacting with a valve head portion to prevent leakage of gas from the cylinder of a piston engine. The edge portion of the slanted valve seat surface may be rounded with a radius of curvature preferably of 0.2~1.0 mm, but more preferably of 0.2~0.5 mm. When the radius of curvature of the rounded edge portion is less than 0.2 mm, the slanted valve seat surface of the ceramic member can be broken by repeated impact applied to the slanted valve seat surface by the valve head. While, when the radius of curvature is more than 1.0 mm, the seating area provided by the slanted valve seat surface is too small to keep the valve seat airtight. The thickness of the side walls of the ceramic member The method of combining both members may be performed by interference fitting, bonding, insert casting or caulking.

The interference fitting may be effected by shrinkage fitting, expansion fitting or press fitting.

The bonding may be effected by means of brazing or diffusion bonding. In this case, it is preferable to metallize the bonding surface of the ceramic member before bonding to the metallic member.

However, the ceramic member can be bonded with the metallic member by using brazing metal containing reactive metal or using reactive metal forming a part of the insert, without metallizing treatment of the surface of the ceramic member.

Among the above mentioned bonding methods, the press fitting is most preferable because it is an easy process.

The dimensions or outer diameters at the opposite ends of the cylindrical ceramic member of the valve seat insert are identical or different to each other according to the metallic member to be combined with the outer cylindrical ceramic member. It is preferable that when the difference between the coefficients of thermal expansion of material of the ceramic member and metallic member of the valve seat insert is small, the dimensions or the outer diameters at the opposite ends of the cylindrical ceramic member are selected to be identical to each other and when the difference between the coefficients of thermal expansion of material of the ceramic member and the metallic member is large, the dimensions or the outer diameters at the opposite ends of the ceramic member are selected to differ from each other. The difference between outer diameters at the opposite ends of the cylindrical ceramic member may be provided by tapering the outer wall of the ceramic member. The taper of the outer wall of the ceramic member is such that the ceramic member does not come out the metallic member at a temperature in use of the valve seat insert.

The valve seat insert of the present invention is secured to the cylinder head by means of the outer metallic member combined with the ceramic member. Accordingly, conventional metal-metal combining methods such as shrinkage fitting, press fitting, screwing into and welding can be used.

BRIEF DESCRIPTION OF THE DRAWINGS

Other objects and advantages are more particularly set forth in the following description and in the accompanying drawings in which:

FIG. 1 is a sectional view of the cylinder head of a piston engine applied the valve seat insert of the present invention; and FIGS. 2-5 are sectional views of various embodiments of the valve seat insert of the invention.

DETAILED DESCRIPTION OF PREFERRED EMBODIMENTS

Referring to FIG. 1, the valve seat insert 20 of the present invention consists of a ceramic member 8 and a metallic member 9 and is secured to the inlet of an exhaust port 4 in the cylinder head 2. The ceramic member 8 of the valve seat insert 20 has a slanted valve seat surface 5 at the end portion of the inner wall thereof for contacting a valve head 6 of a valve 1 if necessary to keep a pressure in the cylinder.

In this embodiment, since the upper end 7 of the valve seat insert 20 is in contact with the cylinder head 2, the ceramic member 8 does not come out of the valve seat insert even if the valve 1 repeatedly impacts against the ceramic member 8.

FIGS. 2-5 show various embodiments of the valve seat insert according to the present invention.

In the embodiment of the valve seat insert shown in FIG. 2, a cylindrical ceramic member 21 of the valve seat insert is integrally combined with an outer cylindrical metallic member 24. The ceramic member 21 has a slanted valve seat surface 27 formed at one end of the inner wall thereof.

The above mentioned valve seat insert may be produced by the following process.

First, a ceramic pipe and a metal pipe each of which has a predetermined outer diameter and inner diameter are prepared. These pipes are cut into a predetermined length of the ceramic member 21 and the metallic member 24. Then, the metallic member 24 is combined around the ceramic member 21 by means of press fitting, shrinkage fitting, brazing, diffusing or caulking to produce a ring of two layers construction consisting of the outer metallic member 24 and the inner metallic member 21. The ring is finally finished into a predetermined outer diameter and cut into a predetermined length.

Alternately, the molten metal for the metallic member is cast around the ceramic pipe to produce a composite pipe constructed of two layers consisting of the outer metal pipe and the inner ceramic pipe. Then, the composite pipe is cut to a predetermined length to provide a combined ring of a two layer construction consisting of the outer metallic member 24 and the inner ceramic member 21. Finally, one end of the inner wall of the ceramic member 21 is chamfered into a slanted valve seat surface 27 having rounded edges of radius of curvature of 0.2~1.0 mm.

The valve seat insert may be used without any finishing of the inner wall surface of the ceramic member.

Referring to FIG. 3 showing another embodiment of the valve seat insert, a cylindrical ceramic member 22 is tapered to provide a difference between outer diameters at the opposite ends thereof and is integrally combined with the cylindrical metallic member 25 around the outer peripheral surface 28 thereof. The end having the smaller outer diameter of the ceramic member 22 is chamfered at the inside thereof to provide a slanted valve seat surface 27.

The valve seat insert shown in FIG. 3 may be produced by the following process.

First, a ceramic pipe and metal pipe each of which has a predetermined outer diameter and inner diameter is prepared. The ceramic pipe is cut into a predetermined length and then tapered on the outer wall thereof to provide the ceramic member 22 having an outer peripheral surface 28. The metal pipe is also cut into a predetermined length of the metallic member 25. Then, the metallic member 25 is combined around the ceramic member 22 by means of press fitting, shrinkage fitting, brazing, diffusion bonding, insert casting or caulking to produce a combined ring of a two layer construction consisting of an outer metal layer and an inner ceramic layer. The ring is finally finished into the predetermined outer diameter and cut into the predetermined length. Furthermore, one end of the ceramic member 22 is chamfered to provide a slanted valve seat surface 27 having rounded edges of radius of curvature of 0.2~1.0 mm.

In the embodiment of the valve seat member shown in FIG. 4, a metallic member 26 is provided with a recess 29 and a cylindrical ceramic member 23 is fitted in the recess and is integral with the metallic member. The ceramic member 23 has a slanted valve seat surface 27 at one end of the inner wall. This valve seat insert may be produced by the following process.

First, the metallic member 26 having the recess 29 and the ceramic member 23 having the predetermined shape and size are prepared. The outer diameter of the ceramic member 23 may be determined according to the method of combining the ceramic member 23 with the metallic member 26. Then, the metallic member 26 is fitted into the recess 29 in the metallic member 26 by means of press fitting, shrinkage fitting, brazing, diffusion bonding or caulking to provide a ring of a two layer construction consisting of an outer metal layer and an inner ceramic layer. The ring is finally finished into the predetermined outer diameter and cut into the predetermined length. Furthermore, one end of the ceramic member 23 is chamfered to provide a slanted valve seat surface 27 having rounded edges of radius of curvature of 0.2~1.0 mm.

Alternately, the molten metal for the metallic member is cast around the ceramic member to produce a composite ring constructed of two layer consisting of the outer metallic member 26 and the inner ceramic member 23. Then, the combined ring is finished into the predetermined outer diameter, inner diameter and length. Finally, one end of the ceramic member 23 is chamfered to provide a slanted valve seat surface 27 inside thereof.

In the embodiment of the valve seat insert shown in FIG. 5, the metallic member 32 has two concentric cylindrical inner walls 35 and 36, while the ceramic member 31 has two concentric cylindrical outer walls 33 and 34 so as to be integrally combined to the metallic member 32. The ceramic member 31 has the slanted valve seat surface 27 being formed at one end of the inner wall thereof and having rounded edges of radius of curvature of 0.2~1.0 mm.

With the above mentioned arrangement of the concentric cylindrical inner wall of the metallic member and the concentric cylindrical outer wall of the ceramic member, the ceramic member is prevented from coming out of the metallic member even if the combined force between the ceramic member and the metallic member is decreased during use.

Furthermore, in the valve seat insert shown in FIG. 5, means for preventing the ceramic member from rotating in the metallic member such as a spring washer or the other resilient member or a fixing pin may be interposed between the upper end 37 of the ceramic member 31 and the cylinder head.

It is noted that when the metallic member of the valve seat insert is made of age-hardenable alloy, the metallic member is combined with the ceramic member under an unage-hardening condition and the combined members are then treated by age-hardening to regulate the hardness of the metallic member into the predetermined hardness before finishing the combined member into the valve seat insert.

EXAMPLE 1

A cylindrical ceramic member having an inner diameter of 43 mm, an outer diameter of 48 mm and a height of 10 mm was made of silicon nitride by pressureless sintering and the opposite circumferential edges of the cylindrical silicon nitride member were formed into rounded edges of a radius of curvature of 1 mm. A cylindrical metallic member made of Incoloy 903 having an inner diameter of 47.4 mm, an outer diameter of 52 mm and a height of 10 mm under a non-hardening condition was press fitted around the cylindrical silicon nitride member at room temperature to produce a cylindrical body having a two layer construction consisting of the inner cylindrical silicon nitride member and the outer Incoloy 903 member. The cylindrical body was kept at a temperature of 718° C. for eight hours and further kept at a lowered temperature of 620° C. for ten hours in a vacuum furnace to harden the cylindrical Incoloy 903 member by age-hardening.

The hardness of Incoloy 903 was increased to HRC42 from HRB90 by the above age-hardening. The age-hardened cylindrical body was cut into a height of 7 mm and then one end of the inner wall of the silicon nitride was chamfered to form a slanted valve seat surface having rounded edges of a radius of curvature of 0.3 mm, thereby producing a valve seat insert having the same shape as shown in FIG. 2.

This valve seat insert was loaded by applying a load of 2000 kg at a temperature of 550° C. and resulted in that the cylindrical silicon nitirde did not come out of the cylindrical Incoloy 903 member.

EXAMPLE 2

The valve seat insert produced in Example 1 was shrinkage fitted into the inlet of exhaust port of cylinder head made of cast iron (having a coefficient of thermal expansion of $13.3 \times 10^{-6}/°C.$, 20°~500° C.) of a single head type diesel engine having a piston cylinder of a diameter of 141 mm to produce a cylinder head as shown in FIG. 1. The diesel engine incorporated with the cylinder head was tested by continuously driving at 1900 rpm. for 1000 hours and resulted in that there was change in both the discharge valve and the valve seat insert.

It is seen from the above description that according to the valve seat insert of the present invention, the brittle ceramic memeber is combined with the metallic member fitted around thereof, so that the ceramic member does not break even if a high impact force is applied during use. Furthermore, the valve seat face is formed in the ceramic member thereby effecting the high wear resistivity, heat shock resistivity and heat resistivity of the ceramic member, while the metallic member makes it easy to fix the valve seat insert to the cylinder head. Furthermore, the difference between the coefficients of thermal expansion of the ceramic member and the metallic member fitted around the ceramic is small, so that after the valve seat insert has been incorporated in the cylinder head, the ceramic member does not come loose or out of the metallic member when the temperature of the valve seat insert increases. Furthermore, according to the valve seat insert of the present invention, when the difference between the coefficients of thermal expansion of the ceramic member and the metallic member is large, the cylindrical ceramic member to be combined with the metallic member is tapered at the outer wall and thereby the decrease in combining force owing to the difference of the coefficient of thermal expansion can be prevented.

What is claimed is:

1. A valve seat insert for use in a cylinder head of a piston engine, comprising a ceramic member being sintered in a substantially cylindrical shape and having a slanted valve seat surface, said surface having a rounded edge portion with a radius of curvature of 0.2–1.0 mm, and a metallic member being integrally combined on a cylindrical outer peripheral wall of the ceramic member and being made of a metallic material having a coefficient of thermal expansion no less than that of the ceramic member and lower than that of the material of the cylinder head.

2. A valve seat insert claimed in claim 1, wherein the cylindrical outer peripheral wall of the ceramic member is tapered.

3. A valve seat insert claimed in claim 1 wherein the ceramic member is made of at least one ceramic material selected from the group consisting of silicon nitride, silicon carbide and sialon, and the metallic member is made of at least one metallic material selected from the group consisting of Fe-Ni alloys, Fe-Ni-Co alloys, Ti and Ti alloys, refractory metal and their alloys, and stainless steel.

4. A cylinder head for a piston engine comprising valve seat inserts incorporated in bores for valves of the piston engine, the valve seat insert consisting of a ceramic member being sintered in a substantially cylindrical shape and having a slanted valve seat surface, said surface having a rounded edge portion with a radius of curvature of 0.2–1.0 mm and a metallic member being integrally combined on the substantially cylindrical outer peripheral wall of the ceramic member and being made of a metallic material having a coefficient of thermal expansion the same as or higher than that of the ceramic member and lower than that of the material of the cylinder head.

5. A cylinder head claimed in claim 4 wherein the cylindrical outer peripheral wall of the ceramic member is tapered.

6. A cylinder head claimed in claim 4, wherein the ceramic member is made of at least one ceramic material selected from the group consisting of silicon nitride, silicon carbide and sialon, and the metallic member is made of at least one metallic material selected from the group consisting of Fe-Ni alloys, Fe-Ni-Co alloys, Ti and Ti alloys, refractory metal and their alloys, and stainless steel.

7. A valve seat insert for use in a cylinder head for a piston engine, comprising a ceramic member being sintered in a substantially cylindrical shape and having a slanted valve seat surface, said valve seat surface having an inner edge of which is rounded with a radius of curvature of 0.2–0.5 mm and a metallic member being integrally combined on the substantially cylindrical outer peripheral wall of the ceramic member and being made of a metallic material having a coefficient of thermal expansion no less than that of the ceramic member and lower than that of the material of the cylinder head.

8. A cylinder head for a piston engine comprising valve seat inserts incorporated in bores for valves of the piston engine, the valve seat insert consisting of a ceramic member being sintered in a substantially cylindrical shape and having a slanted valve seat surface, the inner edge of which is rounded with a radius of curvature of 0.2–0.5 mm and a metallic member being integrally combined on the cylindrical outer peripheral wall of the ceramic member and being made of metallic material having a coefficient of thermal expansion no less than that of the ceramic member and lower than that of the material of the cylinder head.

* * * * *